(12) United States Patent
Baumgartner et al.

(10) Patent No.: US 7,628,815 B2
(45) Date of Patent: Dec. 8, 2009

(54) INTERVERTEBRAL IMPLANT WITH MOVEABLE ENDCAPS

(75) Inventors: Daniel Baumgartner, Oensingen (CH); Mathieu Claude, Bettlach (CH); Adrian Burri, Brig (CH)

(73) Assignee: Synthes USA, LLC, West Chester, PA (US)

( * ) Notice: Subject to any disclaimer, the term of this patent is extended or adjusted under 35 U.S.C. 154(b) by 44 days.

(21) Appl. No.: 10/552,675

(22) PCT Filed: Apr. 11, 2003

(86) PCT No.: PCT/CH03/00240

§ 371 (c)(1), (2), (4) Date: Aug. 15, 2006

(87) PCT Pub. No.: WO2004/089256

PCT Pub. Date: Oct. 21, 2004

(65) Prior Publication Data

US 2007/0073395 A1    Mar. 29, 2007

(51) Int. Cl.
*A61F 2/44* (2006.01)
(52) U.S. Cl. .............. 623/17.15; 623/17.11; 623/17.16; 606/246; 606/279; 606/249
(58) Field of Classification Search .............. 623/17.11, 623/17.16, 17.12, 17.13, 17.14, 17.15; 606/61, 606/246, 249, 252, 279; 403/326, 329; 411/512
See application file for complete search history.

(56) References Cited

U.S. PATENT DOCUMENTS

| | | | |
|---|---|---|---|
| 4,599,086 A * | 7/1986 | Doty | 606/86 A |
| 4,820,305 A | 4/1989 | Harms et al. | 623/16 |
| 4,840,291 A * | 6/1989 | Merlin | 221/59 |
| 5,571,192 A * | 11/1996 | Schonhoffer | 623/17.11 |
| 5,645,606 A | 7/1997 | Oehy et al. | 623/22 |
| 5,702,451 A | 12/1997 | Biedermann et al. | 623/17 |
| 5,713,899 A | 2/1998 | Marnay et al. | 606/61 |
| 5,776,198 A * | 7/1998 | Rabbe et al. | 623/17.15 |
| 6,015,436 A | 1/2000 | Schönhöffer | 623/17 |
| 6,086,613 A * | 7/2000 | Camino et al. | 623/17.16 |
| 6,106,539 A * | 8/2000 | Fortier | 606/185 |

(Continued)

FOREIGN PATENT DOCUMENTS

DE    4012622    7/1991

(Continued)

*Primary Examiner*—Eduardo C Robert
*Assistant Examiner*—Jan Christopher Merene
(74) *Attorney, Agent, or Firm*—Stroock & Stroock & Lavan LLP

(57) ABSTRACT

The invention relates to an anchor piece for fixing an intervertebral implant (15) to the end plate of a vertebra body (19;20), comprising A) an anchor piece (1), with a central axis (6) and two end faces (4, 5) transverse to the central axis (6), B) at least two spikes (7) extending from one of the end faces (4;5), parallel to the central axis (6) and which may be pushed into an end plate of a vertebral body (19;20), whereby B) the anchor piece (1) has a cavity (3) extending through the anchor piece (1) in the direction of the central axis (6) and C) the anchor piece (1) comprises fixing means (9), by means of which the anchor piece may be detachably locked to an intervertebral implant (15).

1 Claim, 4 Drawing Sheets

U.S. PATENT DOCUMENTS

| | | |
|---|---|---|
| 6,176,881 B1 | 1/2001 | Schär et al. |
| 6,193,755 B1 * | 2/2001 | Metz-Stavenhagen et al. .... 623/17.11 |
| 6,193,756 B1 * | 2/2001 | Studer et al. .............. 623/17.15 |
| 6,616,695 B1 * | 9/2003 | Crozet et al. .............. 623/17.11 |
| 6,866,682 B1 * | 3/2005 | An et al. .................. 623/17.15 |
| 6,899,734 B2 * | 5/2005 | Castro et al. ............. 623/17.16 |
| 7,056,343 B2 * | 6/2006 | Schafer et al. ........... 623/17.11 |
| 7,156,874 B2 * | 1/2007 | Paponneau et al. ....... 623/17.11 |
| 7,285,134 B2 * | 10/2007 | Berry et al. .............. 623/17.11 |
| 2001/0056302 A1 * | 12/2001 | Boyer et al. ............. 623/17.15 |
| 2002/0099443 A1 | 7/2002 | Messerli et al. .......... 623/17.11 |
| 2002/0138142 A1 | 9/2002 | Castro et al. |
| 2005/0234550 A1 * | 10/2005 | Metz-Stavenhagen .... 623/17.11 |
| 2008/0161926 A1 * | 7/2008 | Melkent et al. .......... 623/17.16 |
| 2008/0177387 A1 * | 7/2008 | Parimore et al. ......... 623/17.16 |
| 2008/0243254 A1 * | 10/2008 | Butler ..................... 623/17.16 |

FOREIGN PATENT DOCUMENTS

| | | |
|---|---|---|
| DE | 195 09 317 A1 | 9/1996 |
| DE | 19509317 | 9/1996 |
| EP | 0 732 093 A2 | 2/1996 |
| WO | WO 99/32055 | 7/1999 |

* cited by examiner

INTERVERTEBRAL IMPLANT WITH MOVEABLE ENDCAPS

FIELD OF INVENTION

The invention concerns anchoring means for intervertebral implants, as well as an intervertebral implant with two anchoring parts and a method to fasten an intervertebral implant on adjacent bodies of the vertebra.

BACKGROUND OF THE INVENTION

Intervertebral implants, that may be constructed, for example, as intervertebral disc prosthesis and are introduced into the intervertebral space between two adjacent intervertebral discs after the removal of a damaged, natural intervertebral disc or of a damaged nucleus of an intervertebral disc, have to be fixed on the end surfaces of the adjacent bodies of the vertebra, so that the implant could not move with the passage of time. In the fixing of the implant on the end plates of the bodies of the vertebra one differentiates between primary and secondary stabilization. The primary stabilization is necessary immediately following the operation and is preferably carried out by introducing anchoring means, fitted to the implant, into the end plates on the adjacent bodies of the vertebra. The secondary stabilization is achieved by the bone growing on the implant, but one has to reckon with a period of approx. 6 weeks until an adequate fixing of the implant. From U.S. Pat. No. 5,683,465 Shinn an intervertebral disc prosthesis is known, that in one embodiment is fixed on the end plates of the adjacent bodies of the vertebra by means of pins that can pass through the cover plates fitted to the exterior of the implant. It is a disadvantage of this fixing when using these pins, that the pins have to be fastened on the end plates either prior to the introduction of the intervertebral disc prosthesis into the intervertebral space, what during the introduction of the implant into the intervertebral space demands an increased traction of both bodies of the vertebra, or that after the introduction of the implant into the intervertebral space the pins have to be individually pressed into the end plates of the adjacent bodies of the vertebra, resulting in a prolonged operating time.

From U.S. Pat. No. 5,683,465 Shinn an intervertebral disc prosthesis is known, that in one embodiment is fixed on the end plates of the adjacent bodies of the vertebra by means of pins that can pass through the cover plates fitted to the exterior of the implant. It is a disadvantage of this fixing when using these pins, that the pins have to be fastened on the end plates either prior to the introduction of the intervertebral disc prosthesis into the intervertebral space, what during the introduction of the implant into the intervertebral space demands an increased traction of both bodies of the vertebra, or that after the introduction of the implant into the intervertebral space the pins have to be individually pressed into the end plates of the adjacent bodies of the vertebra, resulting in a prolonged operating time.

SUMMARY OF THE INVENTION

This is where the invention wants to provide remedy. The object of the invention is to produce anchoring means for intervertebral implants, that can be brought into a first position for the purpose of introducing the implant in the scraped out intervertebral space, where they do not project with their end past the cover plates and after the introduction of the implant can be brought in a simple manner into a second, lockable position, where the anchoring means are pressed into the end plates of the adjacent bodies of the vertebra and serve the purpose of primary stabilization of the implant.

The invention achieves this objective with anchoring means for intervertebral implants having an anchoring part comprising a central axis and two end faces transverse to the central axis, each anchoring means comprises at least two spikes that protrude past the end faces, are parallel to the central axis and can be pressed into an end plate of a body of the vertebra, characterized in that the anchoring part comprises a hollow space passing through parallel to the central axis, the anchoring part comprises fastening means by means of which the anchoring part can be detachably locked on an intervertebral implant, the intervertebral implant comprises a closing plate each that intersects the central axis, and the closing plates can pass through the hollow spaces in the anchoring parts, as well as a method to fix an intervertebral implant comprising the steps a) enabling the access to the intervertebral space by means of an antero-lateral, ventral lateral, transperitonial or retroperitonial surgical procedure, b) tractioning both bodies of the vertebra adjacent to the intervertebral space, c) scraping out the intervertebral space, d) introducing the intervertebral implant with the anchoring means pushed together, e) moving the anchoring parts axially away from one another until the spikes are adequately pressed into the base plate or the cover plate of the adjacent bodies of the vertebra, and f) fixing the fastening means on the intervertebral implant.

The anchoring means according to the invention serve the purpose of fixing an intervertebral implant on the end plates of bodies of the vertebra and basically comprise an anchoring part with a central axis, a hollow space passing through the anchoring part in the direction of the central axis and two end faces provided transverse to the central axis, at least two spikes that protrude past the end faces and can be pressed into the end plate of a body of the vertebra, and fastening means, by means of which the anchoring means, together with the spikes, can be detachably locked on an intervertebral implant.

The basic advantages, achieved by the invention, are that with the anchoring means according to the invention
  only a minimal traction of two adjacent bodies of the vertebra is necessary when implanting an intervertebral implant into the intervertebral space, and
  by means of the anchoring means according to the invention an intervertebral implant can be simply fixed on the bodies of the vertebra adjacent to the intervertebral implant.

The fastening means can be, for example, snapped in on an intervertebral implant transversely to the central axis of the anchoring means and be elastically deformed, can be pressed or screwed into the anchoring part transversely to the central axis, or executed by a taper joint between the wall of the hollow space and the intervertebral implant.

In a preferred form the fastening means can be elastically deformed transversely to the central axis of the anchoring means and in the non-deformed state protrude into the hollow space in the anchoring part. Elastically deformable fastening means have the advantage, that the anchoring part can be produced in one piece and the danger of losing a component can be avoided.

These fastening means are preferably constructed as hooks with lugs directed towards the central axis.

In another embodiment the fastening means are provided in the hollow space of the anchoring part. This will bring with it the advantage that the anchoring part can be produced without parts axially protruding past the end faces and, for example, the pressing of the spikes into the base plate or cover plate of an adjacent body of the vertebra by means of a suitable surgical instrument will not be hindered by projecting parts.

In yet another embodiment the hooks are so let into the recesses in the wall of the hollow space that is parallel to the central axis, that in the case of the hooks not being deformed transversely to the central axis the lugs of the hooks protrude into the hollow space and in the case of the hooks being deformed transversely to the central axis the hooks, together with their lugs facing the central axis, can be accommodated in the recess, so that an intervertebral implant can be introduced into the hollow space.

In a further embodiment the anchoring part has an annular construction, while the cross-sectional surface of the hollow space at right angles to the central axis and/or the cross-sectional surface of the anchoring part bordered by the external sheathing surface and at right angles to the central axis may be circular surfaces, elliptical surfaces, oval surfaces or polygonal surfaces.

In a preferred embodiment of the intervertebral implant according to the invention it comprises two closing plates at the axial ends, the external surfaces of the closing plates serving the purpose of resting on the cover plate or the base plate of the two adjacent bodies of the vertebra and two anchoring means. The closing plates can be passed through the hollow spaces in the anchoring parts, so that the anchoring parts can be axially displaced relative to the closing plates. The following advantages will be achieved by this:

prior to the introduction of the intervertebral implant into the intervertebral space the anchoring parts can be axially displaced until the spikes do not project past the end faces of the closing plates and thus during the introduction of the intervertebral implant into the intervertebral space the adjacent bodies of the vertebra need only a minimal spreading apart, and after the introduction of the intervertebral implant into the intervertebral space both anchoring parts can be displaced with a simple instrument until the spikes are pressed into the base plate or cover plate of the adjacent bodies of the vertebra.

In a further embodiment the closing plates are mounted without clearance in the hollow spaces of the anchoring parts and can be displaced relative to the closing plates parallel to the central axis. The advantage of this is that after fixing the anchoring means in the base plate or the cover plate of the adjacent bodies of the vertebra the intervertebral implant does not have any radial clearance.

In another embodiment the closing plates comprise second fastening means, in which the fastening means can be engaged on the anchoring parts. These second fastening means can be, for example, that the closing plates of the intervertebral implant have on their sheathing surfaces depressions parallel to the central axis, these depressions serving the purpose of accommodating the lugs of the hooks. The construction with the depressions has the advantage, that by virtue of the lugs snapped into the depressions, the closing plates can be secured against rotation relative to the anchoring parts.

In yet another embodiment the fastening means on the anchoring parts have a clearance relative to the second fastening means on the intervertebral implant, in such a manner that in the case of fixed fastening means small rotations of the anchoring parts about the central axis relative to the closing plates are allowed. This will bring with it the advantage, that torsional movements of the adjacent bodies of the vertebra, that are allowed with a certain range, will be allowed by the connection between the anchoring parts and the intervertebral implant.

In yet another embodiment the second fastening means are such, that the closing plates have axially projecting segments with reduced diameters, so that the lugs of the hooks can snap in.

The method according the invention to fasten an implant, in particular an intervertebral implant on the end plates of both adjacent bodies of the vertebra, basically comprises the following steps:

a) enabling the access to the intervertebral space by means of an anterolateral, ventral lateral, transperitonial or retroperitonial surgical procedure, b) tractioning both bodies of the vertebra adjacent to the intervertebral space, c) scraping out the intervertebral space, d) introducing the intervertebral implant with the anchoring means pushed together. On this occasion both anchoring parts are pushed together until the spikes no longer project past the external surfaces of the closing plates, e) moving the anchoring parts axially away from one another until the spikes are adequately pressed into the base plate or the cover plate of the adjacent bodies of the vertebra, and f) fixing the fastening means on the intervertebral implant. In that case when the fastening means are elastically executed, their fixing is carried out automatically without any action by the surgeon as soon as the anchoring parts are moved apart up to their axial end positions. When the fastening means are, however, constructed as screws or similar means, they have to be fixed with a suitable instrument.

BRIEF DESCRIPTION OF THE SEVERAL VIEWS OF THE DRAWINGS

The invention and developments of the invention are explained in detail in the following based on schematic illustrations of several embodiments. They show in.

DETAILED DESCRIPTION OF THE INVENTION

Figure 1:
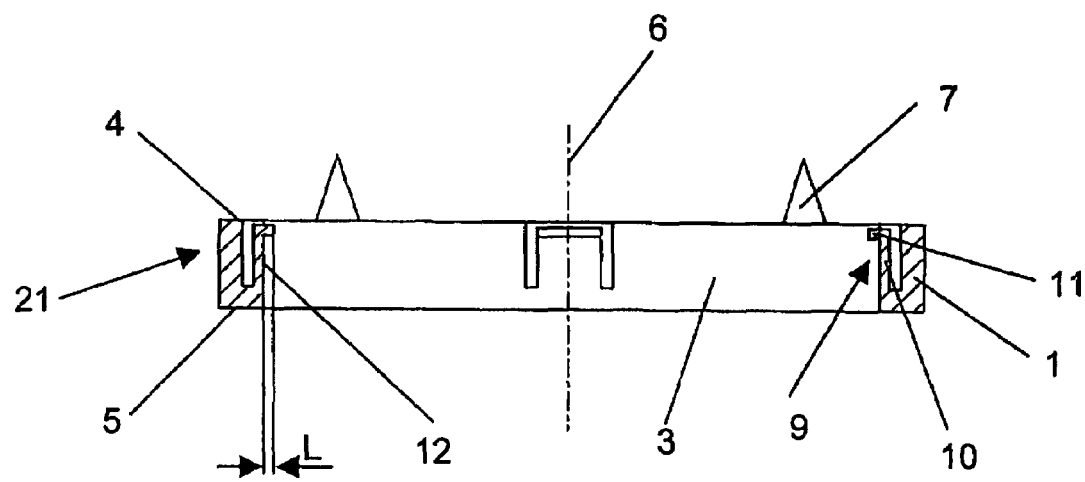
FIG. 1—a section through an embodiment of the anchoring means according to the invention, FIG. 2—a top view on the embodiment of the anchoring means illustrated in FIG. 1, FIG. 3—a section through two anchoring means according to the embodiment illustrated in FIGS. 1 and 2, provided on an intervertebral implant, FIG. 4—a detail of a spinal column with an intervertebral implant implanted and two anchoring means according to the embodiment illustrated in FIGS. 1 and 2, and FIG. 5—a longitudinal section through an intervertebral implant with two anchoring means according to the embodiment illustrated in FIGS. 1 and 2.
Figure 2:
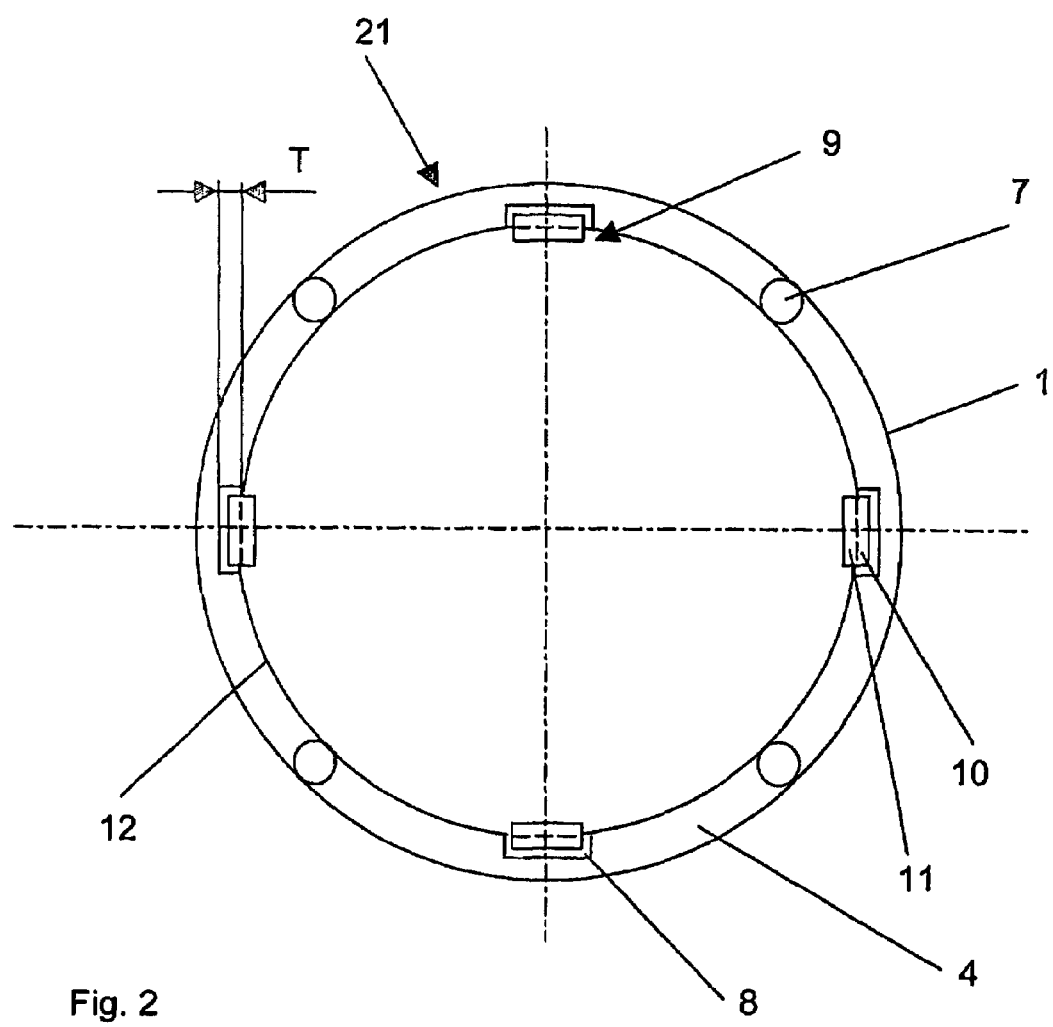
Figure 3:
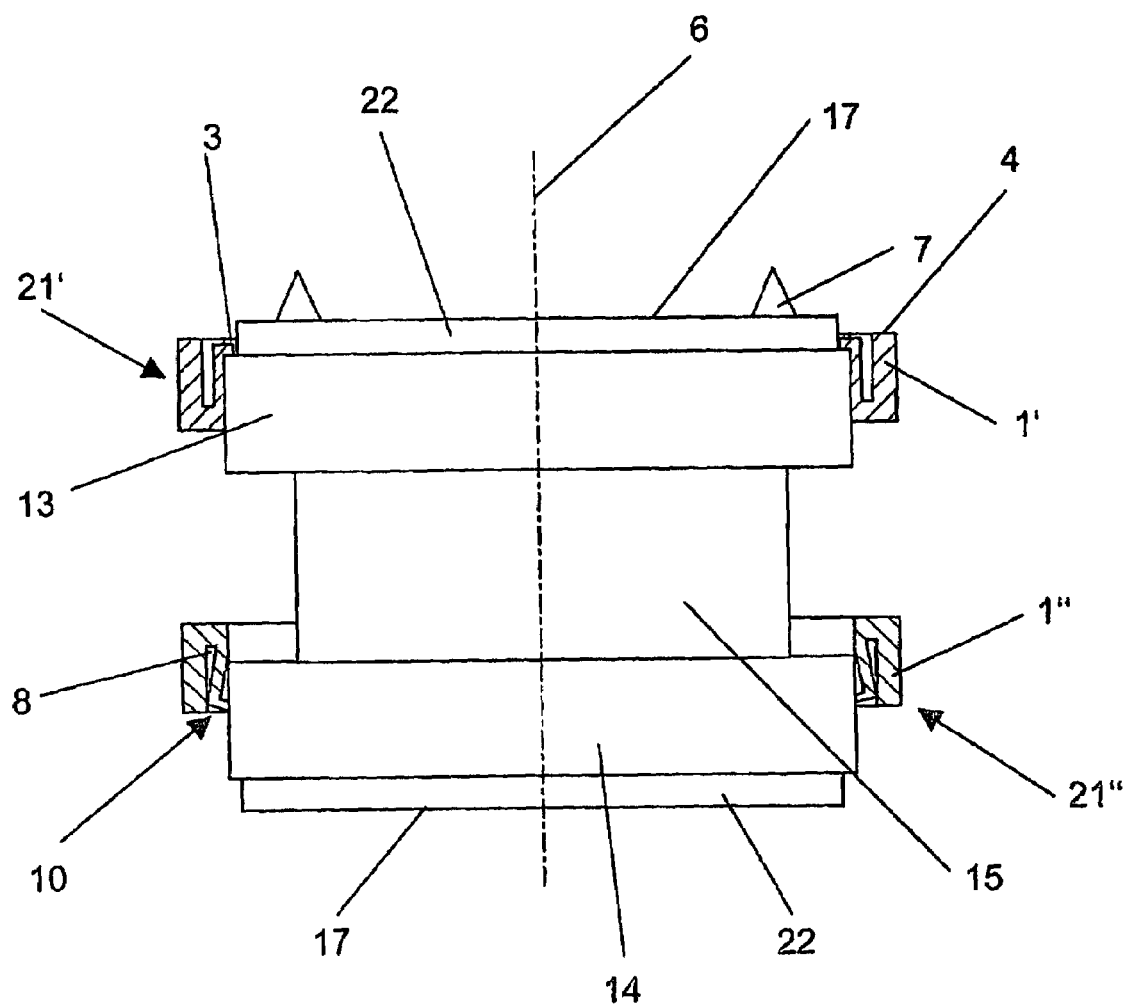

FIGS. 1 and 2 illustrate a preferred embodiment of the anchoring means 21 according to the invention, that basically comprise an anchoring part 1 with a central axis 6 and a hollow space 3 passing through the anchoring part 1 parallel to the central axis 6, a plurality, for example four, spikes 7 parallel to the central axis 6 and fastening means 9. In this case the cross-section of the anchoring part 1 is constructed with a circular cross-section in a plane at right angles to the central axis 6, but it can have an external and/or internal elliptical, oval, reniform or polygonal design, and has a first end face 4 and parallel to it a second end face 5. Both end faces 4, 5 are transversely to the central axis 6. The four spikes 7 are integral with the anchoring part 1 and are perpendicular to the first end face 4. The spikes 7 can be, for example, so constructed, that, as it is illustrated here, they taper towards their free end in the axial direction or they can have a point at their free ends or a convex design, so that during the implantation they can be pressed into the end plate of an adjacent body of the vertebra by displacing the anchoring part 1 parallel to the central axis 6. As fastening means 9 four elastically deformable hooks 10 are provided on the wall 12 of the hollow space parallel to the central axis 6 evenly distributed on the circumference, the lugs 11 of said hooks provided near to the first end face 4 of the anchoring part 3 and protrude into the hollow space 3. With their lugs 11 the hooks 10 can be detachably snapped into an intervertebral implant 15, introduced into the hollow space 3 (FIG. 3). The hooks 10 are so arranged in recesses 8 in the wall 12 of the hollow space, that in the case of non-deformed hooks 10 only the lugs 11 protrude transversely to the central axis 6 into the hollow space 3. Measured perpendicularly to the central axis 6, the recesses 8 have a depth T, whereas the length of the lugs 11, also measured perpendicularly to the central axis 6, is L, while L<T.

FIG. 3 shows two identical anchoring means 21', 21", corresponding to the embodiment described in FIGS. 1 and 2, each of them provided at one end each of an intervertebral implant 15, whereby the spikes 7, arranged on the anchoring parts 1', 1", protrude at the end past the end faces 17 of the intervertebral implant 15. The end faces 17 of the intervertebral implant 15 can be plane, as illustrated here, but they may also dome-shaped. At the same time one anchoring means 21' is illustrated in its second, locked position, while the other anchoring means 21" is in the first position, in which it is pushed parallel to the central axis 6 so far over the intervertebral implant 15, that the spikes 7 do not protrude past the end face 17 of the intervertebral implant 15. When introducing an intervertebral implant 15 into the hollow space 3, the hooks 10 can bend into the recesses 8, so that the intervertebral implant 15 can be pushed through the hollow space 3 parallel to the central axis 6 and past the lugs 11. This is illustrated in the form of an example on the anchoring part 1". In the axial direction the closing plates 13, 14 of the intervertebral implant 15 have at their ends segments 22 with reduced diameters, so that the lugs 11 of the hooks 10 can snap into the shoulder formed by the reduced segments 22 on the closing plates 13, 14. This will achieve that the external end faces 17 of the closing plates 13, 14 will abut against the base plate or the cover plate of the adjacent bodies of the vertebra. Therefore, because the end face 4 of the anchoring part 1 does not abut against the adjacent bodies of the vertebra, it will be ensured that only the intervertebral implant 15 carries the axial load and the load will be transferred to the entire end face 17.

Figure 4:
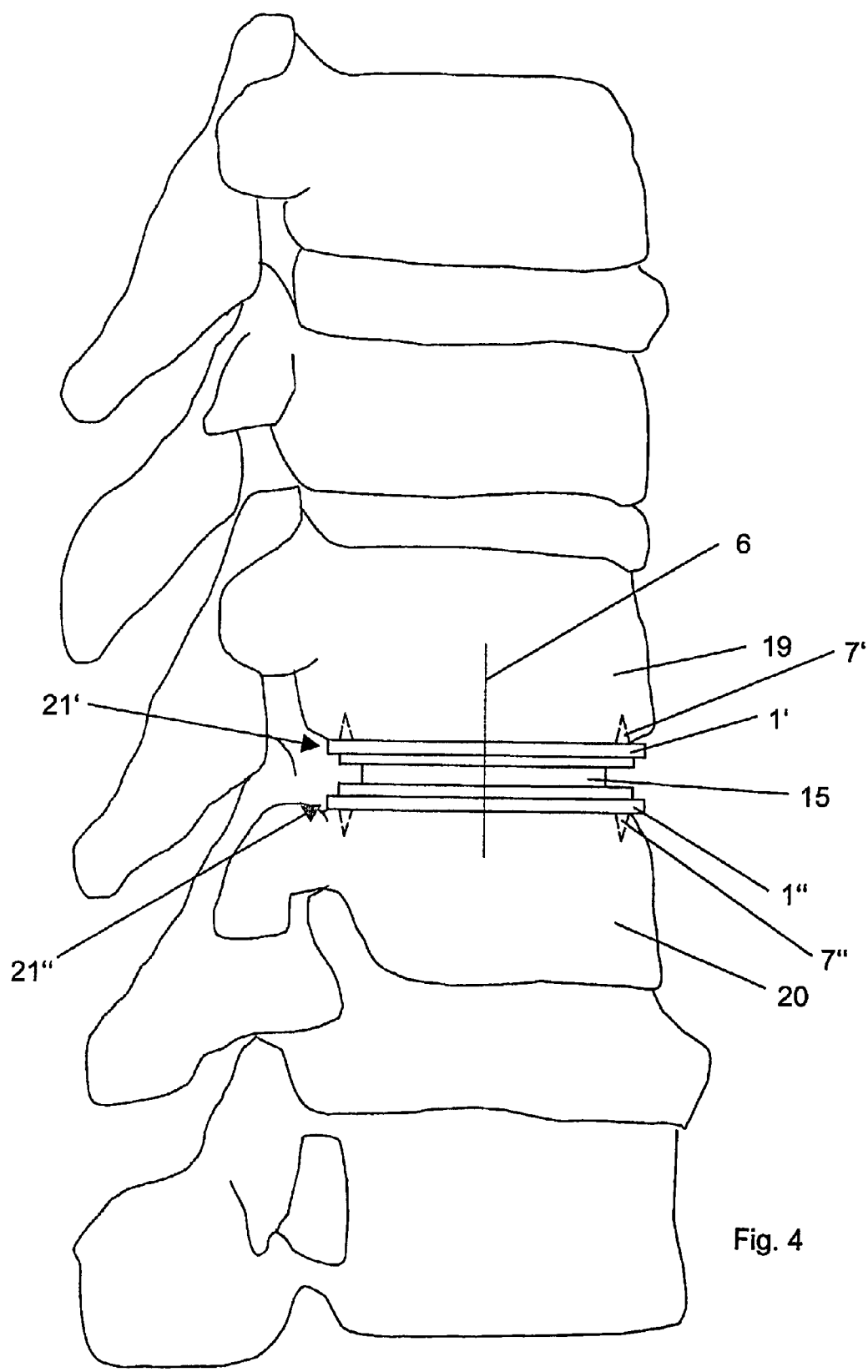

FIG. 4 shows a detail of a spinal column together with an intervertebral implant 15 introduced between two adjacent bodies 19, 20 of the vertebra. The intervertebral implant 15 is fixed on the end plates of the adjacent bodies 1, 20 of the vertebra by anchoring means 21', 21", respectively. For fixing the anchoring means 21', 21" on the bodies 19, 20 of the vertebra the spikes 7', 7" on the anchoring parts 1', 1" are pressed into the end plates of the bodies 19, 20 of the vertebra. When implanting the intervertebral implant 15 into the scraped out intervertebral space, the anchoring parts 1', 1" are pushed over the intervertebral implant 15 so far, that the spikes 7 will not protrude past the end face 17 of the intervertebral implant 15 (FIG. 3). Only after the intervertebral implant 15 together with two anchoring parts 1', 1" are pushed into the scraped out intervertebral space, will the lower and upper anchoring parts 1", 1' be pushed with an expander against the bodies 19, 20 of the vertebra adjacent to the intervertebral implant 15 and the spikes 7 pressed into the end plates of the adjacent bodies 19, 20 of the vertebra. After the spikes 7 had been completely pressed into the end plates and the anchoring parts 1', 1" have reached their end positions, will both hooks 10 (FIG. 2) snap in with their lugs 11, for example, into the end faces 17 of the intervertebral implant, or into the depressions 18 (FIG. 5), complementing the lugs 11, on the sheathing surface 16 of the intervertebral implant 15 that is parallel to the central axis 6.

Figure 5:
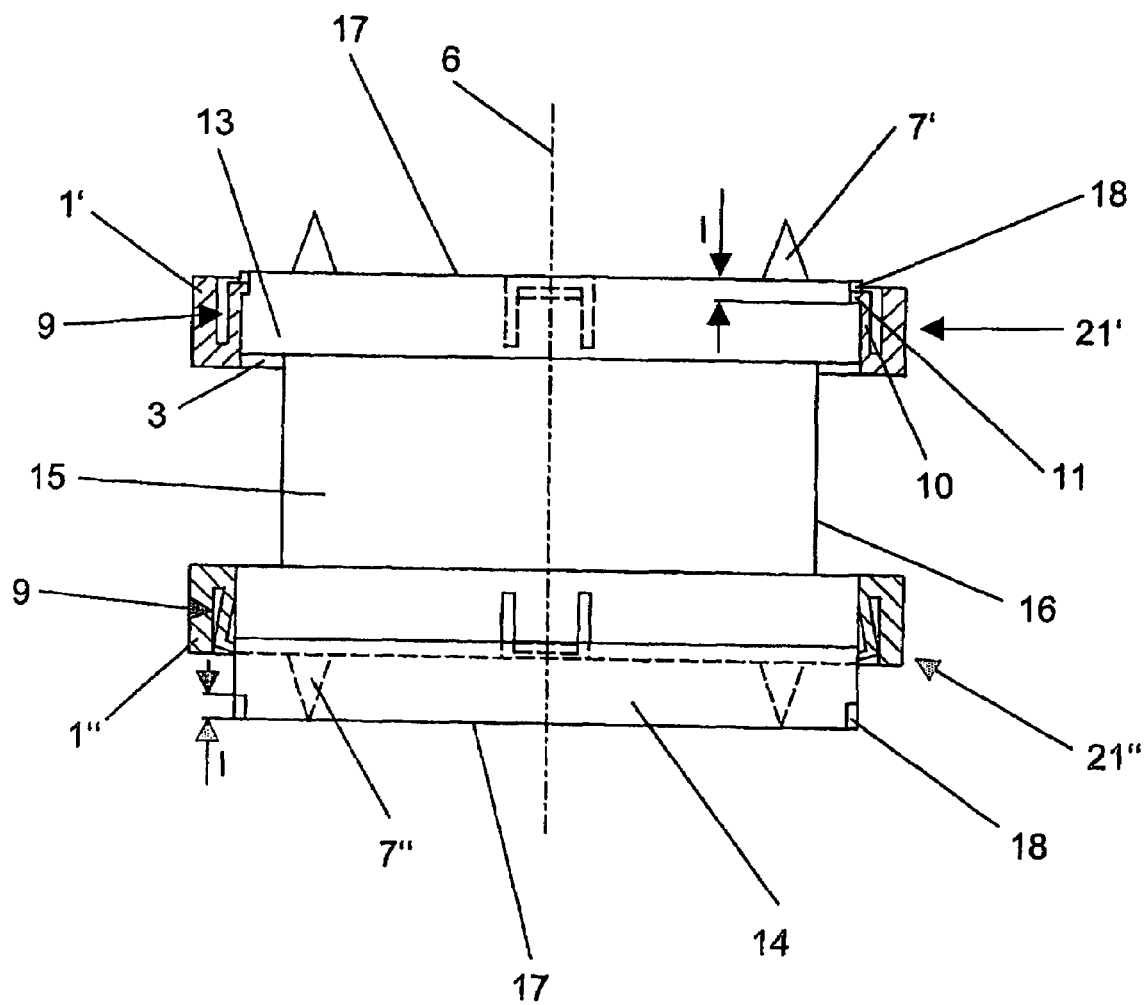

FIG. 5 illustrates an embodiment of an intervertebral implant 15 with anchoring means 21', 21" provided at each axial end. The anchoring means 21', 21" correspond to those described in FIGS. 1 and 2 and comprise an anchoring part 1', 1", respectively, and spikes 7', 7" on the end faces 4 at the axial ends of the anchoring parts 1', 1". The intervertebral implant 15 has at each axial end a closing plate 13, 14, while in their cross-section, that is at right angles to the central axis 6, the construction of the closing plates 13, 14 is complementary to the hollow spaces 3 of the anchoring parts 1', 1". On the external sheathing surface 16 the closing plates 13, 14 are provided with depressions 18, that similarly to the fastening means 9, are distributed on the circumference of the anchoring parts 1', 1" and have a construction to complement the lugs 11 on the fastening means 9. Furthermore, the length of the depressions 18, measured parallel to the central axis 6, is l, and they open at the axial end into the end surfaces 17 of the closing plates 13, 14, that are part of the intervertebral implant 15. The length l is so dimensioned, that in the case of an axial displacement of the anchoring part 21' 21" relative to the end faces 17 of the intervertebral implant 15, the lugs 11 of the hooks 10 will snap into the depressions 18. The externally situated end faces 17 of the intervertebral implant 15 project axially past the end faces 4 of the anchoring parts 1', 1", thus ensuring that the load from both adjacent bodies of the vertebra will be transferred to the intervertebral implant 15 via the end faces 17. The upper anchoring means 21' is illustrated in this case with snapped in fastening means 9, whereas the lower anchoring means 21" on the closing plate 14 is pushed so far on the opposite facing closing plate 14, that the spikes 7" do not protrude past the end face 17 of the intervertebral implant 15. Similarly to FIG. 3, the fastening means 9 of the lower anchoring means 21" are deformed transversely to the central axis 6 and pressed into the depressions 8 in the hollow space 3 of the anchoring part 1".

The invention claimed is:

1. A method of implanting an intervertebral implant into an intravertebral disc space between upper and lower vertebra comprising the steps of:
   a) providing an intervertebral implant including:
      an intervertebral spacer body having an upper endface to contact at least a portion of the upper vertebra and a lower endface to contact at least a portion of the lower vertebra;
      a first end member including a plurality of spikes for engaging at least a portion of the upper vertebra and one or more elastically deformable projections extending from an inner surface of an internal bore formed in the first end member; and
      a second end member including a plurality of spikes for engaging at least a portion of the lower vertebra and one or more elastically deformable projections extending from an inner surface of an internal bore formed in the second end member,
      each of the one or more projections of the first and second end members includes a transversely extending lug for engaging the intervertebral spacer body;
   b) providing access to the intervertebral disc space;
   c) inserting the intervertebral implant into the intervertebral disc space such that the upper endface of the spacer body contacts at least a portion of the upper vertebra and the lower endface of the spacer body contacts at least a portion of the lower vertebra;

d) slidably, non-rotatably moving the first and second end members with respect to the intervertebral spacer body between a second position to a first position;

wherein in the second position: the plurality of spikes formed on the first end member does not extend beyond the upper endface of the spacer body and the pluarality of spikes formed on the second end member does not extend beyond the lower endface of the spacer body, the one or more projections of the first end member are in contact with the inner surface of the internal bore of the first end member, and the one or more projections of the second end member are in contact with the inner surface of the internal bore of the second end member, and in the first position: the plurality of spikes formed on the first end member extend beyond the upper endface of the spacer body and at least partially into engagement with the upper vertebra and the plurality of spikes formed in the second end member extend beyond the lower endface of the spacer body at least partially into engagement with the lower vertebrae, e) securing the position of the first and second end members to the intervertebral spacer body in the first position by the one or more projections of the first end member moving out of contact with the inner surface of the internal bore formed in the first end member and the one or more projections of the second end member moving out of contact with the inner surface of the internal bore formed in the second end member so that the lugs of the one or more projecting members of the first and second end members become engaged to the spacer body.

* * * * *